United States Patent [19]
Cohen

[11] Patent Number: 4,520,024
[45] Date of Patent: May 28, 1985

[54] METHOD OF SELECTIVELY BLOCKING PERIPHERAL VASCULAR SEROTONERGIC RECEPTORS

[75] Inventor: Marlene L. Cohen, Indianapolis, Ind.

[73] Assignee: Eli Lilly and Company, Indianapolis, Ind.

[21] Appl. No.: 465,745

[22] Filed: Feb. 11, 1983

[51] Int. Cl.³ .......................................... A61K 31/495
[52] U.S. Cl. .................................................... 514/255
[58] Field of Search ........................................ 424/250

[56] References Cited

FOREIGN PATENT DOCUMENTS 159713 10/1982 Japan ................................... 424/250

OTHER PUBLICATIONS

Chem. Abs., vol. 42: 1938e (Cerkovnikov et al.).

Primary Examiner—Allen J. Robinson
Assistant Examiner—John M. Kilcoyne
Attorney, Agent, or Firm—James L. Rowe; Arthur R. Whale

[57] ABSTRACT 1-(1-naphthyl)piperazine, a powerful and selective peripheral vascular serotonergic receptor blocker.

1 Claim, No Drawings

METHOD OF SELECTIVELY BLOCKING PERIPHERAL VASCULAR SEROTONERGIC RECEPTORS

BACKGROUND OF THE INVENTION

The existence of peripheral vascular serotonergic receptors ($5HT_2$ type) has recently been demonstrated. The vascular receptor mediating serotonin-induced contraction has now been demonstrated to be of the $5HT_2$ subtype in rat aorta, caudal artery and jugular vein.

Recently, also, it has been postulated that ketanserin, a potent antagonist of $5HT_2$ vascular receptors, acts to lower blood pressure through blockade of these receptors. However, ketanserin also has a high affinity for $alpha_1$ receptors such as that found with phentolamine, another blood pressure lowering agent. At present, there have been no pure peripheral vascular serotonergic receptor blockers available to determine whether such blockade alone would result in anti-hypertensive activity.

SUMMARY OF THE INVENTION

This invention provides a method of blocking peripheral vascular serotonergic receptors in mammals by the administration thereto of 1-(1-naphthyl)piperazine. 1-(1-Naphthyl)piperazine has an extremely high affinity for $5HT_2$ receptors ($-\log K_B = 8.75$) with an approximately 2000 fold lower affinity ($-\log K_B = 5.38$) for alpha-adrenergic receptors. Thus, unlike ketanserin, 1-(1-naphthyl)piperazine has a very high selectivity for $5HT_2$ receptors as a compared with alpha-adrenergic receptors. Bearing this differential affinity in mind, I was able to determine whether administration of 1-(1-naphthyl)piperazine in a dose sufficient to block $5HT_2$ receptors but at a dose insufficient to block alpha receptors would have an effect on blood pressure.

Based upon the experiments which will be described in greater detail below, I was able to determine that selective blockade of $5HT_2$ vascular receptors does not lower blood pressure in conscious spontaneously hypertensive rats (SHR). This conclusion was based on the following laboratory experiment.

Determination of Apparent Dissociation Constants ($-\log K_B$)

Male Wistar rats (150–300 gram weight) were killed and their external jugular veins and thoracic aortas dissected free of connective tissue, cannulated in situ and placed in a modified Krebs' bicarbonate buffer in a suitable tissue bath. Two L-shaped 30-gauge stainless-steel hypodermic needles were inserted in each cannula and the dissected vessels gently pushed onto the needles. One needle was attached with thread to a stationary glass rod and the other to the transducer. [The procedure employed was that described by Hooker, Calkins and Fleisch, *Blood Vessels*, 14, 1, (1977) for use with circular smooth muscle preparations.]

The modified Krebs' bicarbonate buffer had the following makeup: (concentrations in millimoles): sodium chloride, 118.2; potassium chloride, 4.6; calcium chloride dihydrate, 1.6; potassium dihydrogenphosphate, 1.2; magnesium sulfate, 1.2; dextrose, 10.0; sodium bicarbonate, 24.8; and water q.s. to 1000 g. The tissue baths were maintained at 37° C. and were aerated with 95% oxygen-5% $CO_2$. An initial optimum resting force of 1 and 4 g. was applied to the jugular vein and aorta, respectively. Isometric contractions were recorded as changes in grams of force on a Beckman Dynograph with Statham UC-3 transducers and microscale accessory attachment. Tissues were allowed to equilibrate 1 to 2 hours before exposure to drugs. Control responses to serotonin in the jugular vein and to norepinephrine in the aorta were obtained. The vessels were then incubated with appropriate concentrations of antagonist for one hour. Responses to serotonin or to norepinephrine were then repeated in the presence of the antagonist. Contraction to serotonin was evaluated in the jugular vein since this tissue produces marked responses to serotonin in the absence of alpha receptors—see Cohen and Wiley, *J. Pharm. Exp. Ther.*, 205, 400 (1978). Alpha receptor antagonist activity was evaluated in the aorta.

Apparent antagonist dissociation constants were determined for each concentration of antagonist according to the following equation:

$$K_B = \frac{[B]}{[\text{dose ratio} - 1]}$$

wherein [B] is the concentration of the antagonist and the dose ratio is the $ED_{50}$ of the agonist in the presence of the antagonist divided by the control $ED_{50}$. These results are then expressed as the negative logarithm of $K_B$. The $-\log K_B$ values obtained are those for 1-(1-naphthyl)piperazine against $5HT_2$ and alpha adrenergic receptors given above.

IN VIVO STUDIES—CONSCIOUS RATS

Twenty-four week old SHR (325–425 g.) rats were anesthetized with halothane. They were then implanted with femoral arterial and venous catheters. The tips of the arterial and venous catheters were positioned in the abdominal aorta below the renal arteries and lower abdominal vena cava, respectively. The catheters were routed subcutaneously to an exit point at the base of the skull and then through a small leather harness fastened around the forequarters of each animal. The animals were allowed a 3–4 day recovery period after surgery. On the day before a given experiment, the rats to be used in that experiment were conditioned to the experimental surroundings for about 6 hours. In carrying out the determination, the harness on the back of each animal was connected to a spring-tether through which arterial and venous extension tubing were routed. The opposite end of the tubing was connected to a water tight swivel. This system permitted direct recording of blood pressure in conscious, free-moving animals. Mean arterial blood pressure was measured via a Statham strain gauge transducer and recorded on a multichannel oscillograph. The rats were equilibrated for at least 30 minutes prior to the initiation of the experimental protocol. During this equilibration period, the animals preened themselves and the blood pressure was quite labile. After this period, the animals appeared to sleep and pressure was stable. Following a control blood pressure measurement, the rats were dosed with ketanserin, benzoctamine, 1-(1-naphthyl)piperazine or the experimental vehicle via the intraperitoneal route. Blood pressure was monitored at various time intervals after dosing.

Following the above protocol at a 10 mg./kg. dose level, 1-(1-naphthyl)piperazine was ineffective as a blood pressure lowering agent. Ketanserin produced the greatest fall in blood pressure. Benzoctamine lowered blood pressure as did ketanserin but to a lesser degree. The blood pressure reduction paralleled more closely in vitro antagonist potency or affinity for alpha receptors than it did the affinity for vascular $5HT_2$ receptors.

In Vivo Studies—Pithed SHR

SHR were anesthesized with halothane, femoral arterial and venous catheters implanted as before and the trachea cannulated. Each rat was pithed by passing a steel rod through the right orbit and down the entire length of the spinal column. The steel rod remained in place for the duration of the experiment. Immediately after pithing, the rats were ventilated with room air via a rodent respirator which eliminated any anesthetic effects. An equilibration period of 15 minutes was observed prior to control measurements and administration of drugs or vehicle i.p. Increasing doses of serotonin or methoxamine were injected i.v. 15 minutes after the equilibration period. The response was recorded and the blood pressure allowed to recover to control levels. Methoxamine was used because it had a relatively specific alpha$_1$ receptor agonist action, and ketanserin selectively blocks alpha$_1$ receptors. The test drugs were prepared fresh daily and administered by the intraperitoneal route. Benzoctamine and 1-(1-naphthyl)piperazine were administered at a 10 mg./kg. dosage and ketanserin at a 1 mg./kg. dosage. In these experiments, the inhibition of the pressor response to serotonin was greatest for ketanserin followed by 1-(1-naphthyl)piperazine and then benzoctamine, paralleling their in vitro affinities for $5HT_2$ receptors. The inhibition in the pressor response to methoxamine paralleled the in vitro affinity toward alpha receptors, with ketanserin having the greatest effect, benzoctamine second and 1-(1-naphthyl)piperazine the least.

Blood pressure reduction that occurred in the SHR more closely paralleled their alpha adrenergic postsynaptic inhibitory effectiveness (as demonstrated both in vitro and in vivo) than their ability to block peripheral $5HT_2$ receptors.

From the above, it is apparent that 1-(1-naphthyl)piperazine as a peripheral $5HT_2$ receptor blocker is a unique and powerful laboratory tool for the determination of the degree of participation of vascular serotonergic receptors in physiological processes.

In addition, the blocking of $5HT_2$ receptors by 1-(1-naphthyl)piperazine in humans would be useful in those conditions in which an excess of serotonin is present peripherally as in carcinoid syndrome, migraine or some forms of hypertension. In humans, unlike SHR, serotonin purportedly plays a role in hypertension and it has been postulated that the reduction of blood pressure in humans by ketanserin, for example, is due to its ability to block $5HT_2$ receptors rather than its action on alpha-adrenergic receptors. 1-(1-Naphthyl)piperazine, at effective dosages, should have a similar effect on blood pressure. 1-(1-Naphthyl)piperazine is highly selective in its action; i.e., blocks only $5HT_2$ receptors without blocking alpha-adrenergic receptors. It could be used in treating hypertension and would lack the side-effects associated with alpha-receptor blocking drugs. These undesirable side effects include postural hypotension, impotence, tachycardia, and increases in plasma renin.

In utilizing 1-(1-naphthyl)piperazine to block peripheral serotonin receptors in humans having a disease in which excess peripheral serotonin plays a role, the drug can be administered orally, or parenterally. For parenteral administration, the drug can be administered using an acid addition salt, such as the hydrochloride or sulfate, in an isotonic salt solution.

I claim:

1. A process for blocking peripheral vascular serotonergic receptors in living mammals in need of such treatment without blocking alpha$_1$ receptors which comprises administration by the oral or parenteral route to said mammals of a serotonergic receptor blocking amount of 1-(1-naphthyl)piperazine.

* * * * *